United States Patent [19]
Schwarzenbach et al.

[11] 3,944,632
[45] Mar. 16, 1976

[54] PHOSPHORIC ACID ANILIDES
[75] Inventors: Kurt Schwarzenbach, Pfeffingen; Heimo Brunetti, Reinach, both of Switzerland
[73] Assignee: Ciba-Geigy Corporation, Ardsley, N.Y.
[22] Filed: July 31, 1974
[21] Appl. No.: 493,303

[30] Foreign Application Priority Data
Aug. 10, 1973 Switzerland.................... 11564/73
Feb. 6, 1974 Switzerland.................... 1622/74

[52] U.S. Cl....... 260/926; 260/45.7 P; 260/45.95 D; 260/396 N; 260/968; 260/970
[51] Int. Cl.$^2$.................. C07F 9/12; C08K 5/53
[58] Field of Search.................... 260/926

[56] References Cited
UNITED STATES PATENTS
2,965,666  12/1960  Debo et al. ................. 260/926 X

*Primary Examiner*—Anton H. Sutto
*Attorney, Agent, or Firm*—Charles W. Vanecek

[57] ABSTRACT

New processes for the manufacture of alkylated phosphoric acid 4-hydroxyanilides. The compounds, some of which are new, can be used as stabilisers for organic material.

3 Claims, No Drawings

PHOSPHORIC ACID ANILIDES

The present invention relates to new processes for the manufacture of alkylated phosphoric acid 4-hydroxyanilides which are suitable for stabilising organic material against thermo-oxidative degradation.

It is known to employ derivatives of sterically hindered phenols as stabilisers for plastics against thermooxidative degradation or degradation induced by light. It is furthermore known to employ phosphorus derivatives of sterically hindered phenols, in which respect phosphites and phosphonates are prominent.

It is also very customary to employ, for stabilisation, phosphorus compounds as co-stabilisers mixed with phenolic anti-oxidants, and such mixtures often display a synergistic effect. The stabilising action of these classes of compounds or mixtures is, however, often not sufficiently strong to suppress lastingly the degradation of plastics under conditions of use. In addition, esters of phosphoric acid and of phosphorous acid are easily hydrolysable compounds, which makes them difficult to store and leads to acid decomposition products, which in turn can promote the degradation of polymer materials. It has now been found that the phosphoric acid anilides of the general formula I are surprisingly stable, storage-stable compounds, the action of which as stabilisers is substantially better than that of the abovementioned phosphorus-containing, sterically hindered phenols.

The manufacture of such phosphoric acid anilides by reacting optionally substituted anilines with phosphoric acid diester-halides is known. This method has the disadvantage that it is often necessary to use aniline derivatives which are sensitive to oxidation, and are therefore difficult to store, as the starting compounds.

Furthermore, the preparation and use of phosphoric acid diester-halides require a large technical effort. These compounds are usually prepared by halogenating dialkyl phosphites, which makes it necessary to destroy, or to process separately, the hydrogen halide action produced. In addition, the phosphoric acid diester-halides are processed by distillation and must be stored with exclusion of moisture.

The processing of phosphoric acid anilides prepared by the known process often leads to difficulties, because deeply coloured impurities — oxidation products of the aniline derivatives used — have to be separated off.

Surprisingly, a new process has now been found which does not have these disadvantages.

In the process according to the invention, phosphoric acid anilides of the formula I

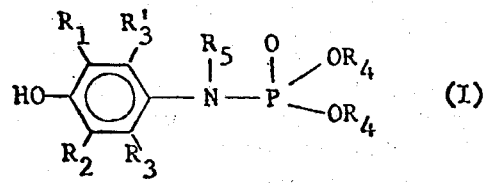

are prepared by reacting a compound of the formula II

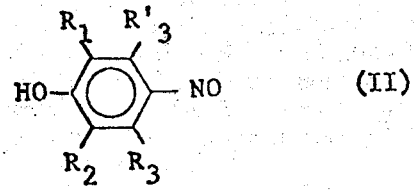

with a phosphorous acid ester of the formula III $$P(OR_4)_3 \quad (III);$$

in the compounds of the formula I to III,
$R_1$ denotes a straight-chain or branched alkyl group, a cycloalkyl group or an aralkyl group, $R_2$ denotes hydrogen, a straight-chain or branched alkyl group, a cycloalkyl group or an aralkyl group, $R_3$ and $R_3'$ independently of one another denote hydrogen or a lower alkyl group, $R_4$ denotes a straight-chain or branched alkyl group, a substituted alkyl group, a cycloalkyl group, a thiaalkyl group or an aralkyl group, and $R_5$ denotes hydrogen or the group

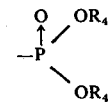

Those compounds in which $R_5$ denotes the group

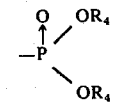

are new.

In the process according to the invention compounds of the formula I are preferably prepared in which $R_1$ and $R_2$ independently of one another denote a straight-chain or branched alkyl group with 1 – 5 carbon atoms or cycloalkyl with 6 – 8 carbon atoms, $R_3$ and $R_3'$ denote hydrogen, $R_4$ denotes a straight-chain or branched alkyl group with 1 – 8 carbon atoms or benzyl, and $R_5$ denotes hydrogen or the group

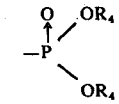

Compounds of the formula I are particularly preferentially prepared in which $R_1$, $R_2$ and $R_4$ independently of one another denote alkyl, such as, for example, for $R_1$ and $R_4$, alkyl with 1 to 4 carbon atoms, and for $R_2$, alkyl with 3 or 4 carbon atoms, $R_3$ and $R_3'$ denote hydrogen and $R_5$ denotes hydrogen or the group

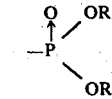

In the definition of the compounds of the formula I, $R_1$ and $R_2$ can be alkyl groups, such as, for example, methyl, ethyl, isopropyl, butyl, sec. butyl, tert. butyl, amyl, tert. amyl or sec. amyl, and $R_4$ can denote an alkyl group, such as, for example, methyl, ethyl, isopropyl, butyl, sec. butyl, tert. butyl, amyl, tert. amyl, sec. amyl, hexyl, octyl, 1,1,3,3-tetramethylbutyl, decyl, dodecyl, tetradecyl, hexadecyl, octadecyl, eicosyl or docosyl. $R_3$ and $R_3'$ can denote lower alkyl groups, such as alkyl with 1 to 4 carbon atoms, such as methyl, ethyl, n-propyl, isopropyl, n-butyl or isobutyl.

$R_1$, $R_2$ and/or $R_4$ can also be a cycloalkyl group, such as, for example, cyclopentyl, cyclohexyl, α-methylcyclohexyl or cyclooctyl, or an aralkyl group, such as benzyl, α-phenylethyl or α,α-dimethylbenzyl.

$R_4$, in the sense of substituted alkyl, can be halogenoalkyl, preferably chloroalkyl or bromoalkyl, such as 2-chloroethyl, 2-bromoethyl or 2-chlorobutyl.

As thiaalkyl, $R_4$ can denote, for example, 3-thiabutyl, 3-thiapentyl, 3-thiaundecyl, 3-thiapentadecyl, 3-thiaheneicosyl, 4-thiapentyl, 4-thiahexyl, 4-thiahexadecyl or 4-thiadocosyl.

The process according to the invention for the manufacture of phosphoric acid anilides possesses various advantages in comparison with the previously known process. Firstly, it is possible to employ the stable and storable nitroso compounds of the formula II as well as the easily accessible phosphites of the formula III. In this way two process stages are eliminated, namely the reduction of the nitroso compounds of the formula II to the corresponding amines on the one hand, and the preparation of the phosphoric acid diester-halides on the other hand. Secondly, the reaction products of the formula I are obtained free from coloured impurities.

The reaction of trialkyl phosphites with nitro compounds or nitroso compounds has hitherto been used for the synthesis of heterocyclic nitrogen compounds. The applicability of the reaction to nitroso-phenols, which can exsist in a tautomeric form as quinone oximes, and the formation of phosphoric acid amides as main products, could not have been foreseen.

The process according to the invention can be carried out in the absence or in the presence of a solvent. If solvents are used, it is advantageous to select aliphatic or aromatic hydrocarbons or higher-boiling ethers, the boiling points of which are above 100°C, since at lower temperatures the reaction velocity falls to practically zero. The solvent can be, for example, toluene, xylene, mesitylene, tetralin, decalin, ligroin or a higher-boiling petroleum fraction.

The reaction can be carried out in the absence or in the presence of a catalyst. If catalysts are used, the yields are improved and the products are obtained in a higher state of purity. Acid catalysts are preferably used, the boiling points of which are above the boiling point of the solvent used, for example organic acids such as acetic acid, chloroacetic acid, propionic acid or benzoic acid, or inorganic acids such as phosphorous acid or phosphoric acid.

The phosphites of the formula III are used in excess, preferably in a 2-fold to 20-fold molar excess, relative to the nitroso compounds of the formula II. The use of a 5-fold to 10-fold molar excess is particularly preferred, if the reaction is carried out without a solvent.

The temperatures in the process according to the invention are not critical. They are important only for the rate at which the reaction proceeds. If lower molecular trialkyl phosphites of the formula II are used, the reaction is preferably carried out at the boiling point of the trialkyl phosphite used. 150°–200°C is the temperature range particularly preferred.

The reaction according to the invention is preferably carried out under nitrogen or a noble gas, at normal pressure. It is possible, for example, to mix all the components at room temperature and then to heat subsequently for one-half to 20 hours, depending on the reaction temperature. In individual cases it can be advantageous to heat the solvent, phosphite and, optionally, a catalyst and to add the nitroso compound to the hot solution.

The starting products of the formulae II and III are known or can be prepared easily by generally known methods.

The present invention also relates to a process for the manufacture of the new compounds of the formula Ia

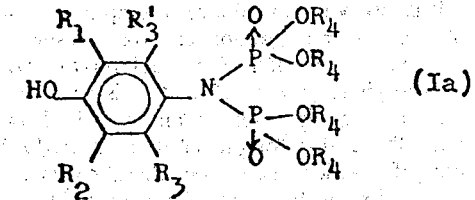

wherein $R_1$ denotes a straight-chain or branched alkyl group, a cycloalkyl group or an aralkyl group, $R_2$ denotes hydrogen, a straight-chain or branched alkyl group, a cycloalkyl group or an aralkyl group, $R_3$ and $R_3'$ independently of one another denote hydrogen or a lower alkyl group, and $R_4$ denotes a straight-chain or branched alkyl group, substituted alkyl group, a cycloalkyl group, a thiaalkyl group or an aralkyl group.

The compounds of the formula Ia represent a subgroup of the compounds of the formula I.

This process is characterised in that a compound of the formula IV

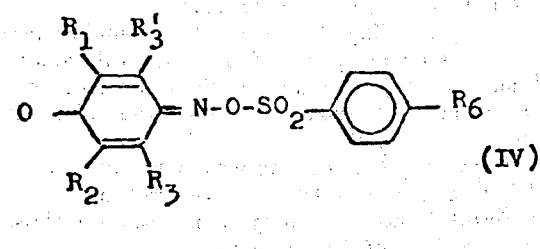

in which $R_6$ denotes hydrogen, methyl or bromine, is reacted in an aprotic solvent with 2 mols of a compound of the formula V

wherein $Me^\oplus$ has the meaning of $Li^\oplus$, $Na^\oplus$ or $K^\oplus$.

In this process it is preferable to prepare compounds of the formula Ia in which $R_1$ and $R_2$ independently of one another denote a straight-chain or branched alkyl group with 1 – 5 carbon atoms or cycloalkyl with 6 14 8 carbon atoms, $R_3$ and $R_3'$ denote hydrogen and $R_4$ denotes a straight-chain or branched alkyl group with 1 – 8 carbon atoms or benzyl.

It is particularly preferable to pepare compounds of the formula Ia in which $R_1$, $R_2$ and $R_4$ independently of one another denote alkyl, such as, for example, alkyl with 3 or 4 carbon atoms for $R_1$ and $R_2$ or ethyl for $R_4$, and $R_3$ and $R_3'$ denote hydrogen.

The reaction is carried out at room temperature. Examples of suitable solvents are: benzene, toluene, xylene, hexane, petroleum ether, ligroin, tetrahydrofurane, dioxane, ethylene glycol dimethyl ether or ethylene glycol diethyl ether.

The reaction is preferably carried out in such a way that a dialkyl phosphite of the formula VI

is initially placed in the selected solvent and is converted into the salt of the formula V by means of about 1 mol equivalent of a base such as, for example, an alkali metal amide or an alkali metal hydride. This solution is then reacted in the same solvent, at room temperature, with a solution containing about 0.5, preferably 0.4 to 0.5, mol equivalent of a compound of the formula IV.

The compounds of the formula I obtained by the process according to the invention are also suitable as flameproofing agents for organic polymers, especially for fibre-forming polyesters.

The starting products of the formula IV are in turn new compounds, which are prepared in a manner which is in itself known from the compounds of the formula II by reaction in a molar ratio with a compound of the formula VII

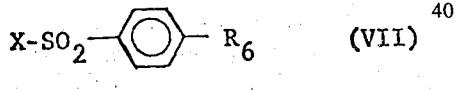

wherein X denotes halogen, preferably chlorine. The reaction is carried out in the presence of one mol equivalent of a tertiary amine, normally in a solvent.

Examples of compounds of the formula I are:
phosphoric acid dibenzyl ester 3,5-ditert.butyl-4-hydroxyanilide,
phosphoric acid bis(2-chloroethyl ester) 3,5-ditert.butyl-4-hydroxyanilide,
phosphoric acid diethyl ester 3-tert.butyl-4-hydroxy-5,6-dimethylanilide,
phosphoric, acid diethyl ester 3,5-bis-α-methylbenzyl-4-hydroxyanilide,
phosphoric acid dioctadecyl ester 3,5-ditert.butyl-4-hydroxyanilide,
3,5-ditert.butyl-4-hydroxyphenyl-imido-bis-(phosphoric acid dibenzyl ester) and
3-tert.butyl-4-hydroxy-5,6-dimethylphenyl-imido-bis-(phosphoric acid dioctyl ester).

The compounds of the formula I are used as stabilisers for organic substrates. Possible examples of the latter are:

1. Polymers which are derived from hydrocarbons with single or double unsaturation, such as polyolefines, such as, for example, polyethylene, which can be optionally crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylene-propylene copolymers, propylene-butene-1 copolymers, propylene-isobutylene copolymers, styrene-butadiene copolymers and terpolymers of ethylene and propylene with a diene, such as, for example, hexadiene, dicyclopentadiene or ethylidene-norbornene; mixtures of the abovementioned homopolymers, such as, for example, mixtures of polypropylene and polyethylene, polypropylene and polybutene-1, or polypropylene and polyisobutylene.

2. Vinyl polymers containing halogen, such as polyvinyl chloride, polyvinylidene chloride, polyvinyl fluoride, but also polychloroprene and chlorinated rubbers.

3. Polymers which are derived from α,β-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, polyallyl melamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.
8. Polyurethanes and polyureas.
9. Polycarbonates.
10. Polysulphones.
11. Polyamides and copolyamides which are derived from diamines and dicarboxylic acids and/or from aminocarboxylic acids or the corresponding lactams, such as polyamide 6, polyamide 6/6, polyamide 6/10. polyamide 11 and polyamide 12.

12. Polyesters which are derived from dicarboxylic acids and dialcohols and/or from hydroxycarboxylic acids or the corresponding lactones, such as polyethylene glycol terephthalate or poly-1,4-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerol-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as crosslinking agents, and also their halogen-containing modifications of low inflammability.

16. Natural polymers such as cellulose, rubber, proteins and their polymer-homologously chemically modified derivatives, such as cellulose acetates, cellulose propionates and cellulose butyrates, or the cellulose ethers, such as methylcellulose.

17. Natural and synthetic organic substances which are pure monomeric compounds or mixtures of such, for example mineral oils, animal and vegetable fats, oils and waxes, or oils, waxes and fats based on synthetic esters and mixtures of synthetic esters with mineral oils in any desired weight ratios.

The compounds of the formula I are incorporated in the substrates in a concentration of 0.005 to 5% by weight, relative to the material to be stabilised.

Preferably, 0.01 to 1.0, particularly preferably 0.02 to 0.5, % by weight of the compounds, relative to the material to be stabilised, are incorporated into the latter. The incorporation can be carried out, for example, by mixing in at least one of the compounds of the formula I and optionally further additives by the methods customary in the art, before or during shaping, or by applying the compounds, dissolved or dispersed, to the polymer, where appropriate with subsequent evaporation of the solvent.

In the case of crosslinked polyethylene, the compounds are added before the crosslinking.

The compounds of the formula I can also be added before or during the polymerisation, it being possible, by a potential incorporation into the polymer chain, to obtain stabilised substrates in which the stabilisers are not volatile or capable of extraction.

The following may be mentioned as examples of further additives with which the stabilisers can be conjointly employed:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2 Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxyanisole, tris-(3,5-di-tert.-butyl-4-hydroxyphenyl)-phosphite, 3,5-di-tert.-butyl-4-hydroxyphenyl-stearate and bis-(3,5-di-tert.-butyl-4-hydroxyphenyl)-adipate.

1.3 Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.

1.4 Alkylidene-bisphenols, such as, for example, 2,2'-methylene-bis-(6-tert.-butyl-4-methylphenol),2,2'-methylene-bis-(6-tert.butyl-4-ethylphenol), 4,4'-methylene-bis-(6-tert. butyl-2-methylphenol), 4,4'-methylene-bis-(2,6-di-tert. butyl-phenol), 2,6-di-(3-tert.butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)butane, 1,1-bis-(5-tert.butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert. butyl-4-hydroxy-2-methylphenyl)-4-n-dodecylmercapto-butane, 1,1,5,5-tetra-(5-tert.butyl-4-hydroxy-2-methylphenyl)-pentane and ethylene glycol-bis-[3,3-bis-(3'-tert.butyl-4'-hydroxyphenyl)-butyrate].

1.5 O-, N- and S-benzyl compounds, such as, for example, 3,5,3',5'-tetra-tert.butyl-4,4'-dihydroxydibenzyl ether; 4-hydroxy-3,5-dimethylbenzyl-mercaptoacetic acid octadecyl ester, tris-(3,5-di-tert.butyl-4-hydroxybenzyl)-amine and bis-(4-tert.butyl-3-hydroxy-2,6-dimethylbenzyl)-dithioterephthalate.

1.6 Hydroxybenzylated malonic esters, such as, for example, 2,2-bis-(3,5-di-tert.butyl-2-hydroxybenzyl)-malonic acid dioctadecyl ester, 2-(3-tert.butyl-4-hydroxy-5-methylbenzyl)-malonic acid dioctadecyl ester, 2,2-bis-(3,5-di-tert. butyl-4-hydroxybenzyl)-malonic acid di-dodecylmercapto-ethyl ester and 2,2-bis-(3,5-di-tert.butyl-4-hydroxybenzyl)malonic acid di-[4-(1,1,3,3-tetramethylbutyl)-phenyl] ester.

1.7 Hydroxybenzyl-aromatics, such as, for example, 1,3,5-tri-(3,5-di-tert.butyl-4-hydroxybenzyl)-2,4,6-trimethylbenzene, 1,4-di-(3,5-di-tert.butyl-4-hydroxybenzyl)-2,3,5,6-tetramethylbenzene and 2,4,6-tri-(3,5-di-tert.butyl-4-hydroxybenzyl)-phenol.

1.8 s-Triazine compounds, such as, for example, 2,4-bis-octylmercapto-6-(3,5-di-tert.butyl-4-hydroxy-anilino)-s-triazine, 2-octylmercapto-4,6-bis-(3,5-di-tert.butyl-4-hydroxy-anilino)-s-triazine, 2-octylmercapto-4,6-bis-(3,5-di-tert.butyl-4-hydroxy-phenoxy)-s-triazine, 2,4,6-tris-(3,5-di-tert.butyl-4-hydroxyphenoxy)-s-triazine, 2,4,6-tris-(3,5-di-tert.butyl-4-hydroxyphenylethyl)-s-triazine and 1,3,5-tris-(3,5-di-tert.butyl-4-hydroxybenzyl)-isocyanurate.

1.9 Amides of β-(3,5-di-tert.butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-(3,5-di-tert.butyl-4-hydroxyphenyl-propionyl)-hexamethylenediamine.

1.10. Esters of β-(3,5-di-tert.butyl-4-hydroxyphenyl)-propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]octane.

1.11. Esters of β-(5-tert.butyl-4-hydroxy-3-methylphenyl propionic acid with monohydric or polyhydric alcohols, such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo [2,2,2]octane.

1.12. Esters of 3,5-di-tert.butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo [2,2,2]octane.

1.13. Acylaminophenols, such as, for example, N-(3,5-di-tert. butyl-4-hydroxyphenyl)-stearic acid amide and N,N'-di-(3,5-di-tert.butyl-4-hydroxyphenyl)-thiobis-acetamide.

1.14. Benzylphosphonates, such as, for example, 3,5-di-tert. butyl-4-hydroxybenzyl-phosphonic acid dimethyl ester, 3,5-di-tert.butyl-4-hydroxybenzyl-phosphonic acid diethyl ester, 3,5-di-tert.butyl-4-hydroxybenzyl-phosphonic acid dioctadecyl ester and 5-tert.butyl-4-hydroxy-3-methylbenzyl-phosphonic acid dioctadecyl ester.

1.15. Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-sec. butyl-p-phenylenediamine, 6-ethoxy-2,2,4-trimethyl-1,2-dihydroquinoline, 6-dodecyl-2,2,4-trimethyl-1,2-dihydroquinoline, monooctyliminodibenzyl and dioctyliminodibenzyl and polymerised 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.octyl-p-phenylene-diamine, N,N'-di-(1,4-dimethylpentyl)-p-phenylenediamine, N,N'-dimethyl-N,N'-di-(sec.octyl)-p-phenylenediamine, 2,6-dimethyl-4-methoxyaniline, 4-ethoxy-N-sec.butylaniline, the condensation product of diphenylamine and acetone, and phenothiazine.

2. UV absorbers and light protection agents 2.1 2-(2'-Hydroxyphenyl)-benztriazoles, such as, for example, the 5'-methyl-, 3',5'-di-tert.butyl-, 5'-tert.butyl-, 5'-(1,1, 3,3-tetramethylbutyl)-, 5-chloro-3',5'-di-tert.butyl-, 5-chloro-3'-tert.butyl-5'-methyl-, 3'-sec.butyl-5'-tert.butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.amyl-, 3'-methyl-5'-carbomethoxyethyl- and 5-chloro-3',5'-di-tert.-amyl-derivative.

2.2. 2,4-Bis-(2'-hydroxyphenyl)-6-alkyl-s-triazines, such as, for example, the 6-ethyl-, 6-heptadecyl or 6-undecyl-derivative.

2.3. 2-Hydroxy-benzophenones, such as, for example, the 4-hydroxy-, 4-methoxy-, 4-octoxy-, 4-decyloxy-, 4-dodecyloxy-, 4-benzyloxy, 4,2',4'-trihydroxy- or 2'-hydroxy-4,4'-dimethoxyderivative.

2.4. 1,3-Bis-(2'-hydroxy-benzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids, such as, for example, phenyl salicylate, octylphenyl salicylate, dibenzoylresorcinol, bis-(4-tert.-butylbenzoyl)-resorcinol, benzoylresorcinol and 3,5-di-tert.-butyl-4-hydroxybenzoic acid 2,4-di-tert.butyl-phenyl ester, octadecyl ester or 2-methyl-4,6-di-tert.butyl-phenyl ester.

2.6. Acrylates, such as, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester and N-(β-carbomethoxy-vinyl)-2-methyl-indoline.

2.7. Nickel compounds, such as, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel complexes of bis-[2-hydroxy-4-(1,1,3,3,-tetramethylbutyl)-phenyl]-sulphone, such as the 2:1 complex, optionally with additional ligands such as 2-ethyl-caproic acid, nickel dibutyldithiocarbamate, nickel salts of 4-hydroxy-3,5-di-tert.butylbenzyl-phosphonic acid monoalkyl esters, such as of the methyl, ethyl or butyl ester, nickel complexes of ketoximes such as of 2-hydroxy-4-methyl-phenyl-undecylketonoxime, nickel 3,5-di-tert.butyl-4-hydroxy-benzoate and nickel isopropylxanthate.

2.8. Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl) sebacate, and 3-n-octyl-7,7,9,9-tetramethyl-1,3,8-triaza-spiro[4,5]decane-2,4-dione.

2.9. Oxalic acid diamides, such as, for example, 4,4'-di-octyloxy-oxanilide, 2,2'-di-octyloxy-5,5'-di-tert.butyl-oxanilide, 2,2'-di-dodecyloxy-5,5'-di-tert.butyl-oxanilide, 2-ethoxy-2'-ethyl-oxanilide, N,N'-bis-(3-dimethylaminopropyl)-oxalamide, 2-ethoxy-5-tert.butyl-2'-ethyl-oxanilide and its mixture with 2-ethoxy-2'-ethyl-5,4'-di-tert.butyl-oxanilide and mixtures of ortho- and para-methoxy- as well as of o- and p-ethoxy-disubstituted oxanilides.

3. Metal deactivators, such as, for example, oxanilide, isophthalic acid dihydrazide, sebacic acid bis-phenylhydrazide, bis-benzylidene-oxalic acid dihydrazide, N,N'-diacetyl-adipic acid dihydrazide, N,N'-bis-salicyloyloxalic acid dihydrazide, N,N'-bis-salicyloyl-hydrazine, N,N'-bis-(3,5-di-tert.butyl-4-hydroxyphenyl-propionyl)-hydrazine, N-salicylal-N'-salicylidenehydrazine and 3-salicyloylamino-1,2,4-triazole.

4. Phosphites, such as, for example, triphenyl phosphite, diphenylalkyl phosphites, phenyldialkyl phosphites, tri-(nonylphenyl) phosphite, trilauryl phosphite, trioctadecyl phosphite, 3,9-di-isodecyloxy-2,4,8,10-tetroxa-3,9-diphosphaspiro[5,5]undecane and tri-(4-hydroxy-3,5-di-tert.butylphenyl) phosphite.

5. Compounds which destroy peroxides, such as, for example, esters of β-thiodipropionic acid, for example the lauryl, stearyl, myristyl or tridecyl esters, mercaptobenzimidazole and the zinc salt of 2-mercapto-benzimidazole.

6. Polyamide stabilisers, such as, for example, copper salts in combination with iodides and/or phosphorous compounds and salts of divalent manganese.

7. Basic co-stabilisers, such as, for example, melamine, benzoguanamine, polyvinylpyrrolidone, dicyandiamide, triallyl cyanurate, urea derivatives, hydrazine derivatives, amines, polyamides, polyurethanes, and alkali metal salts and alkaline earth metal salts of higher fatty acids, for example Ca stearate, Zn stearate, Mg stearate, Na ricinoleate, K palmitate, antimony pyrocatecholate or zinc pyrocatecholate.

8. PVC stabilisers, such as, for example, organic tin compounds, organic lead compounds and barium-cadmium salts of fatty acids.

9. Nucleating agents, such as, for example 4-tert.butyl-benzoic acid, adipic acid and diphenylacetic acid.

10. Urea derivatives, such as, for example, N-cyclohexyl-N'-1-naphthylurea, N-phenyl-N,N'-dicyclohexylurea, N-phenyl-N'-2-naphthylurea, N-phenylthiourea, N,N'-dibutylthiourea.

11. Other additives, such as, for example, plasticisers, lubricants, emulsifiers, fillers, carbon black, asbestos, kaolin, talc, glass fibres, pigments, optical brighteners, flameproofing agents and antistatic agents.

The preparation and use of the compounds according to the invention are described in greater detail in the examples which follow. In these, parts denote parts by weight and % denotes percentages by weight.

EXAMPLE 1

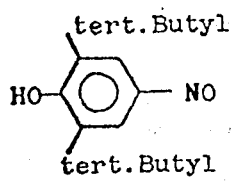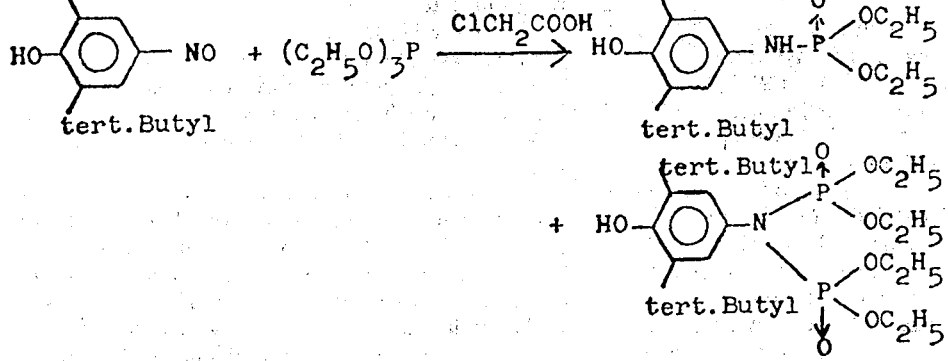

23.5 g (0.1 mol) of 2,6-ditert.butyl-4-nitrosophenol, 9.4 g (0.1 mol) of chloroacetic acid, 166 g (1 mol) of triethyl phosphite and 500 ml of decalin are mixed.

The mixture is heated at 160°C for 2 hours. After cooling and allowing to stand overnight, the colourless, crystalline precipitate is filtered off with suction, ground with a little water and once more filtered off and rinsed with a little hexane. The mother liquor is concentrated to 20 ml, treated with hexane and allowed to stand for some hours. During this time a further quantity of the product is slowly precipitated. The two lots of crystals (35 g) are combined and are recrystallised from cyclohexane. After drying the product has a melting point of 127°C. Nuclear magnetic resonance spectroscopic analysis and column chromatographic separation show that the product is a mixture of 30% of phosphoric acid diethyl ester 3,5-ditert.butyl-4-hydroxyanilide (melting point 162°C in the pure state after chromatographic separation) and 70% of 3,5-ditert.butyl-4-hydroxyphenyl-imido-bis-(phosphoric acid diethyl ester) (melting point 140°C in the pure state after chromatographic separation).

EXAMPLE 2

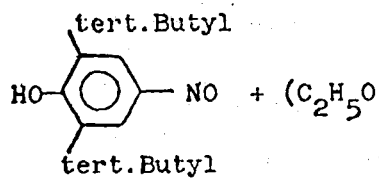

30 g (0.18 mol) of triethyl phosphite, 1.9 g (0.02 mol) of chloroacetic acid and 100 ml of decalin are heated together to 160°C. 4.7 g (0.02 mol) of 2,6-ditert.butyl-4-nitrosophenol are added all at once into the hot solution and the mixture is stirred for a further 30 minutes and then cooled. Phosphoric acid diethyl ester 3,5-ditert.butyl-4-hydroxyanilide (2.5 g) is precipitated from the mixture in a practically pure form after some hours. The product can be recrystallised from hexane and melts at 162°C.

EXAMPLE 3

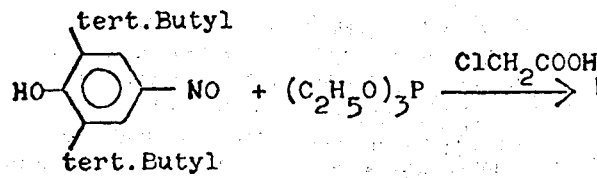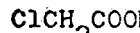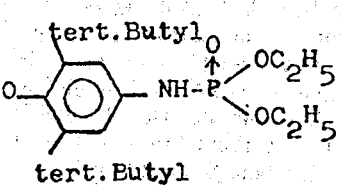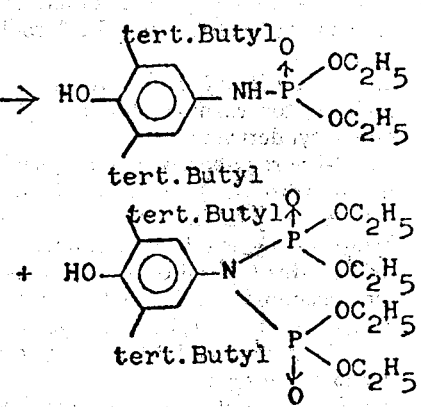

4.7 g (0.02 mol) of 2,6-ditert.butyl-4-nitrosophenol, 4.1 g (0.05 mol) of phosphorous acid and 30 g (0.18 mol) of triethyl phosphite in 50 ml of decalin are heated for 2 hours at 160°C. After cooling, the excess triethyl phosphite is distilled off in a high vacuum and the residue is treated with hexane. After half an hour the preciptated crystals are filtered off with suction (7.2 g). After recrystallisation from cyclohexane the product has a melting point of 132°C. The product consists of approximately 30% of phosphoric acid diethyl ester 3,5-ditert.butyl-4-hydroxyanilide and approximately 70% of 3,5-ditert.butyl-4-hydroxyphenyl-imido-bis-(phosphoric acid diethyl ester), as is shown by the nuclear magnetic resonance spectroscopic analysis.

EXAMPLE 4

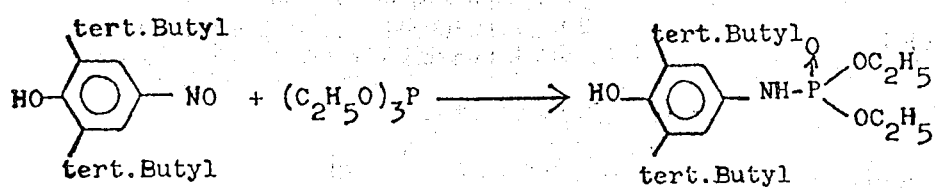

4.7 g (0.02 mol) of 2,6-ditert.butyl-4-nitrosophenol and 30 g (0.18 mol) of triethyl phosphite are dissolved in 100 ml of anisole and the mixture is heated for 2 hours at 150°C. Excess solvent and triethyl phosphite are then distilled off in a high vacuum. The residue which crystallises is ground with hexane, allowed to stand for a short time, filtered off and dried. It has a melting point of 150°C. The product is phosphoric acid diethyl ester 3,5-ditert.butyl-4-hydroxyanilide, contaminated with small quantities of 3,5-ditert.butyl-4-hydroxyphenyl-imido-bis-(phosphoric acid diethyl ester).

The same result is obtained if mesitylene or a petroleum fraction boiling at approx. 170°C is used as the solvent instead of anisole.

EXAMPLE 5

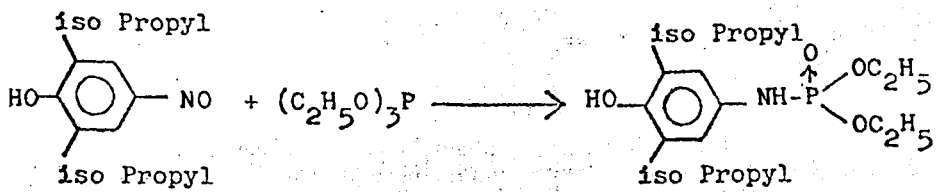

4.1 g (0.02 mol) of 2,6-di-isopropyl-4-nitrosophenol, 1,9 g (0.02 mol) of chloroacetic acid, 30 g (0.18 mol) of triethyl phosphite and 100 ml of decalin are mixed. The mixture is heated for 2 hours at 160°C. After cooling, excess triethylphosphite and the solvent are distilled off in vacuo and the residue is separated by column chromatography. On eluting with a mixture of 98% of chloroform and 2% of methanol, phosphoric acid diethyl ester 3,5-diisopropyl-4-hydroxyanilide is obtained, which, after recrystallisation from cyclohexane, has a melting point of 158° C.

If 2,6-di-isopropyl-4-nitrosophenol is replaced in this example by an equivalent quantity of 2-tert.butyl-4-nitroso-6-methylphenol, an otherwise identical procedure gives phosphoric acid diethyl ester 3-tert.butyl-4-hydroxy-5-methylanilide of melting point 151°C.

EXAMPLE 6

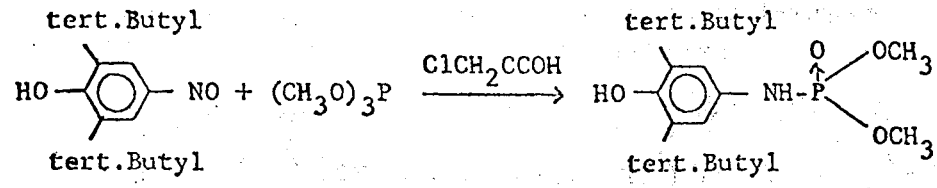

4.7 g (0.02 mol) of 2,6-ditert.butyl-4-nitrosophenol, 1.9 g (0.02 mol) of chloroacetic acid, 30 g of trimethyl phosphite and 100 ml of toluene are mixed and boiled under reflux for 3 hours. After cooling and allowing to stand overnight, the colourless, crystalline precipitate is filtered off with suction and washed with a little water and then with hexane. The product has a melting point of 165°–170°C. Analysis by thin layer chromatography and separation by column chromatography show that the product consists of approximately equal parts of phosphoric acid dimethyl ester 3,5-ditert.butyl-4-hydroxyanilide (melting point 204°C in the pure state after chromatographic separation) and 3,5-ditert.butyl- 4-hydroxyphenyl-imido-bis-(phosphoric acid dimethyl ester) (melting point 186°C in the pure state after chromatographic separation).

EXAMPLE 7

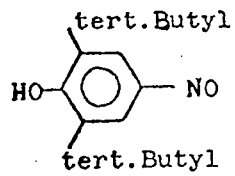 + 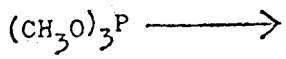 → 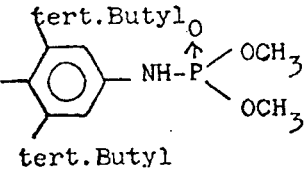

5 g (0.021 mol) of 2,6-ditert.butyl-4-nitrosophenol are dissolved in 25 g (0.2 mol) of trimethyl phosphite. The mixture is boiled under reflux for 14 hours. After cooling, it is evaporated and the residue is treated with hexane. The crystals (3.2 g) of phosphoric acid dimethyl ester 3,5-ditert.butyl-4-hydroxyanilide which have precipitated have a melting point of 204°C.

EXAMPLE 8

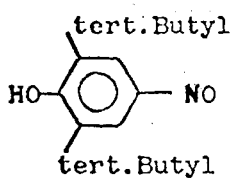 +  → 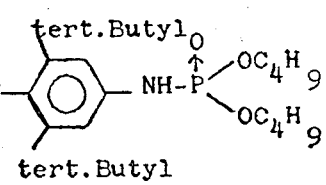

5 g (0.021 mol) of 2,6-ditert.butyl-4-nitrosophenol in 30 g (0.12 mol) of tri-n-butyl phosphite are heated for 3 hours at 150°C. After cooling, the excess tri-n-butyl phosphite is distilled off under high vacuum. The residual oil (10 g) is separated on silica gel by column chromatography. 6 g of phosphoric acid di-n-butyl ester 3,5-ditert.butyl-4-hydroxyanilide are eluted by means of a mixture of 98% of chloroform and 2% of methanol. After recrystallisation from hexane, the product has a melting point of 127°C.

EXAMPLE 9

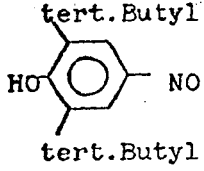 +  → 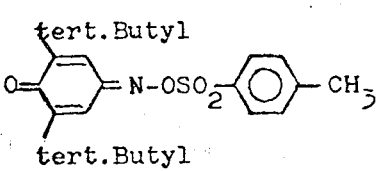

270 g (1.15 mols) of 2,6-ditert.butyl-4-nitrosophenol are dissolved in 2.5 liters of dimethylacetamide. A solution of 256 g (1.35 mols) of p-toluenesulphonic acid chloride in 1.1 liters of dimethylacetamide is added dropwise at room temperature. 112 g (1.10 mols) of triethylamine are then added rapidly and the mixture is stirred for 2 hours at 80°C. After cooling, it is poured into 15 liters of water and the precipitated product is filtered off. After drying it is recrystallised from hexane. 298 g of 2,6-ditert.butyl-benzoquinone monoxime p-toluenesulphonate of melting point 110°C are thus obtained.

If 2,6-ditert.butyl-4-nitrosophenol is replaced in this example by an equivalent quantity of 2,6-diisopropyl-4-nitrosophenol, an otherwise identical procedure gives 2,6-diisopropyl-benzoquinone monoxime p-toluenesulphonate of melting point 93°C.

EXAMPLE 10

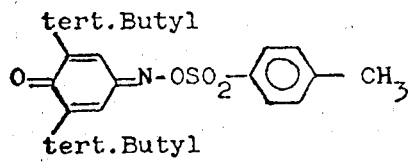 → 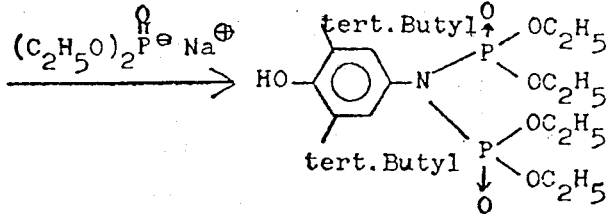

15.0 g (0.11 mol) of diethyl phosphite are initially placed in 150 ml of absolute toluene. After adding 2.4 g (0.1 mol) of sodium hydride, the mixture is heated to 60°C and stirred until the sodium hydride has dissolved. The solution is cooled to room temperature and a solution of 19 g (0.049 mol) of 2,6-ditert.butyl-benzoquinone monoxime p-toluenesulphonate in 50 ml of toluene is added dropwise. After stirring for a further 2 hours at 60°C, 50 ml of water are added and the toluene solution is separated off, thoroughly washed several times with water and dried. The crystalline residue which remains after evaporation is twice recrystallised from cyclohexane. 14.9 g of 3,5-ditert.butyl-4-hydroxyphenylimido-bis-(phosphoric acid diethyl ester) of melting point 140°C are thus obtained.

If 2,6-ditert.butyl-benzoquinone monoxime p-toluene-sulphonate is replaced in this example by an equivalent quantity of 2,6-diisopropyl-benzoquinone monooxime p-toluene-sulphonate, an otherwise identical procedure gives, after evaporating the toluene solution, a yellow-red oil, the main component of which is isolated by column chromatography. The product is liquid and consists, according to elementary analysis, of 3,5-diisopropyl-4-hydroxyphenyl-imido-bis(phosphoric acid diethyl ester).

Analysis: $C_{20}H_{37}O_7NP_2$: Calculated: C 51.6; H 8.0; P 13.3; Found: C 50.9; H 8.1; P 14.0

EXAMPLE 11

Stabilisation of polybutadiene rubber 100 parts of polybutadiene ("Solprene 250" of Messrs. Phillips), which is pre-stabilised with 0.75% of 2,6-ditert.butyl-p-cresol, are kneaded additionally for 30 minutes in a Brabender plastograph at 150°C at 60 r.p.m. with 0.1 part of stabilisers shown in Table 1. During this time the resistance to kneading is continuously recorded in the form of the torque. A maximum torque occurs as a result of crosslinking which takes place initially, and subsequent degradation. The effectiveness of the stabilisers manifests itself in a reduction of the maximum value of the torque.

The gel content determined after the Brabender treatment counts as a further criterion of the protective action of the stabilisers which have been incorporated. For this purpose, 1 g of the sample is dissolved in 100 ml of toluene overnight at room temperature. These solutions are filtered through glass wool, the particles of gel retained are rinsed with a little toluene and the filtered solutions are evaporated to dryness and the residue dried to constant weight. The gel content of a sample is obtained by the following calculation:

Gel content in % $[(E-A)/E] \cdot 100$
$E$ = total weight of the sample examined
$A$ = weight of the dissolved component.

Table 1

| Stabiliser from Example No. | Maximum value of torque in grams × meters | Gel content after 30 minutes, % |
|---|---|---|
| Without stabiliser | 3,625 | 44 |
| 1 | 2,500 | 0 |
| 2 | 2,375 | 0 |
| 5 | 2,875 | 10 |
| 10 | 2,975 | 13 |

EXAMPLE 12

Stabilisation of styrene-butadiene rubber (SBR)

100 parts of styrene-butadiene rubber (SBR 1502 of Messrs. Hüls) are kneaded for 30 minutes in a Brabender plastograph at 150°C and 60 r.p.m. with 0.1 part of each of the stabilisers shown in Table 2. During this time the resistance to kneading is recorded continuously in the form of the torque. A maximum torque occurs as a result of crosslinking which takes place initially, and subsequent degradation. The effectiveness of the stabilisers manifests itself in a reduction of the maximum value of the torque.

The gel content determined after the Brabender treatment counts as a further criterion of the protective action of the stabilisers which have been incorporated. For this purpose, 1 g of the sample is dissolved in 100 ml of toluene overnight at room temperature. These solutions are filtered through glass wool, the particles of gel retained are rinsed with a little toluene and the filtered solutions are evaporated to dryness and dried to constant weight. The gel content of a sample is obtained by the following calculation:

Gel content in %: $[E-A)/E] \cdot 100$
$E$ = total weight of the sample examined
$A$ = weight of the dissolved component.

Table 2

| Stabiliser from Example No. | Maximum value of torque in grams × meters | Gel content after 30 minutes, % |
|---|---|---|
| Without stabiliser | 2,975 | 47 |
| 1 | 2,700 | 25 |
| 2 | 2,250 | 3 |
| 5 (Melting point 151°C) | 2,740 | 30 |

EXAMPLE 13

Flameproofing of polyethylene terephthalate 15 parts of a commercially available polyethylene terephthalate are dissolved in 85 parts of hexafluoroisopropanol. This solution is mixed with 0.75 or 1.5 parts of the stabiliser of Example 10 [3,5-ditert.-butyl-4-hydroxy-phenyl-imido-bis-(phosphoric acid diethyl ester)] and is stirred until homogeneous and half the solution is spread out in a thickness of 0.5 mm on a glass plate by means of a rod for drawing film. A glass fabric is then laid upon it and pressed on lightly. The second half of the coating composition is cast thereon and adjusted to a thickness of 1 mm by means of guide rings of this thickness. Drying is then carried out in vacuo for 16 hours at 60°C. The stabilisers are therefore present in the films in a concentration of 5 or 10%.

The dried film is lifted off the glass plate and the combustibility of these films is then determined by the LOI method described by C.P. Fenimore and J.F. Martin in Combustion and Flame 10, No.2, 135–139 (June 1966). In this the film is ignited in an atmosphere of nitrogen and oxygen of varying composition by volume and the volume ratio at which combustion of the test samples can just be maintained is determined. The LOI value is the minimum oxygen concentration in a nitrogen-oxygen mixture at which the test sample still just burns. The higher the LOI value, the lower is the combustibility of the film, that is to say the more effective is the flameproofing additive.

The results thus obtained are summarised in Table 3 which follows:

Table 3

| Flameproofing agent | Quantity | LOI |
|---|---|---|
| Stabiliser from Example 10 | 5% | 0.219 |
|  | 10% | 0.236 |
| Without flameproofing agent | — | 0.200 |

What we claim is:
1. A compound of the formula Ia

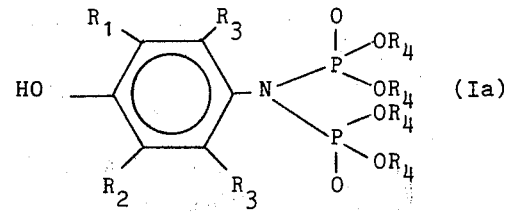

in which $R_1$ and $R_2$ independently of one another are a straight-chain or branched alkyl group of 1–5 carbon atoms or cycloalkyl of 6–8 carbon atoms, $R_3$ and $R_3$ are hydrogen and $R_4$ is a straight-chain or branched alkyl group of 1–8 carbon atoms or benzyl.
2. Compounds according to claim 1, characterised in that, in the formula Ia, $R_1$ and $R_2$ denote tert.butyl, $R_3$ and $R_3'$ denote hydrogen and $R_4$ denotes methyl or ethyl.
3. The compound according to claim 1, of the formula
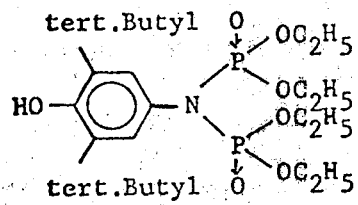
* * * * *